United States Patent
Kosecoff

(10) Patent No.: US 11,798,057 B2
(45) Date of Patent: Oct. 24, 2023

(54) DEVICE FOR MEASURING HAIR EXPOSURE TO HARMFUL LIGHT AND RECOMMENDING PERSONALIZED HAIRCARE PRODUCTS

(71) Applicant: L'Oreal, Paris (FR)

(72) Inventor: David B. Kosecoff, San Francisco, CA (US)

(73) Assignee: L'Oreal, Paris (FR)

( * ) Notice: Subject to any disclaimer, the term of this patent is extended or adjusted under 35 U.S.C. 154(b) by 267 days.

(21) Appl. No.: 17/084,235

(22) Filed: Oct. 29, 2020

(65) Prior Publication Data

US 2022/0138827 A1    May 5, 2022

(51) Int. Cl.
  *G06Q 30/00*  (2023.01)
  *G06Q 30/0601*  (2023.01)
  *A45D 44/00*  (2006.01)
  *G01N 33/50*  (2006.01)

(52) U.S. Cl.
  CPC ....... *G06Q 30/0631* (2013.01); *A45D 44/005* (2013.01); *G01N 33/5014* (2013.01); *G06Q 30/0621* (2013.01); *A45D 2044/007* (2013.01)

(58) Field of Classification Search
  None
  See application file for complete search history.

(56) References Cited

U.S. PATENT DOCUMENTS 10,365,156 B2    7/2019  Gonzalez et al.
10,918,328 B2 *  2/2021  Mueller ............... A61B 5/0082
2012/0320191 A1* 12/2012 Meschkat ............. G01N 21/84
                                                        348/135
2015/0041663 A1*  2/2015 Oliver ..................... G01W 1/00
                                                        250/372
2015/0102208 A1   4/2015  Appelboom et al.
(Continued)

FOREIGN PATENT DOCUMENTS

FR      2865278 A1 *  7/2005  ............. G01N 33/84
WO   2015/051013 A1    4/2015
(Continued)

OTHER PUBLICATIONS

Ana Carolina Santos Nogueira et al; "Hair color changes and protein damage caused by ultraviolet radiation" Apr. 9, 2004; Journal of Photochemistry and Photobiology B: Biology 74 (2004) 109-117 (Year: 2004).*

(Continued)

*Primary Examiner* — Michelle T Kringen
*Assistant Examiner* — Norman Donald Sutch, Jr.
(74) *Attorney, Agent, or Firm* — Christensen O'Connor Johnson Kindness PLLC

(57) ABSTRACT

A computer system and the computer-implemented method of generating and providing haircare product recommendations to a subject. The method comprises determining, by a computing device, an exposure amount of light impacting a subject's hair; determining, by the computing device, a damage assessment of the subject's hair based on the type of light and amount of light exposure; and providing, by the computing device, at least one haircare product recommendation to the subject, wherein the recommendation is directed to repair damage to the hair provided in the damage assessment.

6 Claims, 4 Drawing Sheets

(56) References Cited

U.S. PATENT DOCUMENTS

| | | | |
|---|---|---|---|
| 2015/0177055 A1 | 6/2015 | Lian et al. | |
| 2017/0191866 A1* | 7/2017 | Balooch | G01J 1/029 |
| 2018/0017437 A1* | 1/2018 | Poutiatine | G01J 1/0228 |
| 2018/0374567 A1 | 12/2018 | Toumazou et al. | |
| 2019/0051135 A1 | 2/2019 | Semanoukian et al. | |
| 2019/0204146 A1* | 7/2019 | Wei | G01J 1/0219 |
| 2021/0401360 A1* | 12/2021 | Metten | A61B 5/742 |

FOREIGN PATENT DOCUMENTS

| | | | | |
|---|---|---|---|---|
| WO | WO-2015166403 A1 * | 11/2015 | | A45D 44/005 |
| WO | 2019/036589 A1 | 2/2019 | | |
| WO | 2020/142728 A1 | 7/2020 | | |
| WO | 2021/003344 A1 | 1/2021 | | |

OTHER PUBLICATIONS

Venta Air Technologies "How to Protect Your Hair From Harmful Air Pollution", https://venta-usa.com/protect-hair-air-pollution, 5 pages.

Sebetić et al. "UV Damage of the Hair", Coll. Antropol., vol. 32, Suppl. 2, pp. 163-165 (2008).

French Search Report and Written Opinion dated Oct. 1, 2021, issued corresponding French Application No. 2100576, filed Jan. 21, 2021, see p. 1 of 7 pages.

International Search Report and Written Opinion dated Jan. 27, 2022, issued in corresponding PCT Application No. PCT/US2021/055519, filed Oct. 19, 2021, 14 pages.

International Preliminary Report on Patentability, dated May 11, 2023, in corresponding International Patent Application No. PCT/US2021/055519, 8 pages.

* cited by examiner

DEVICE FOR MEASURING HAIR EXPOSURE TO HARMFUL LIGHT AND RECOMMENDING PERSONALIZED HAIRCARE PRODUCTS

SUMMARY

Personal sensor product that measures exposure of hair to harmful light, assesses possible damage caused by different types of harmful light and recommends more personalized set of haircare products targeted to repair the damage done to hair.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
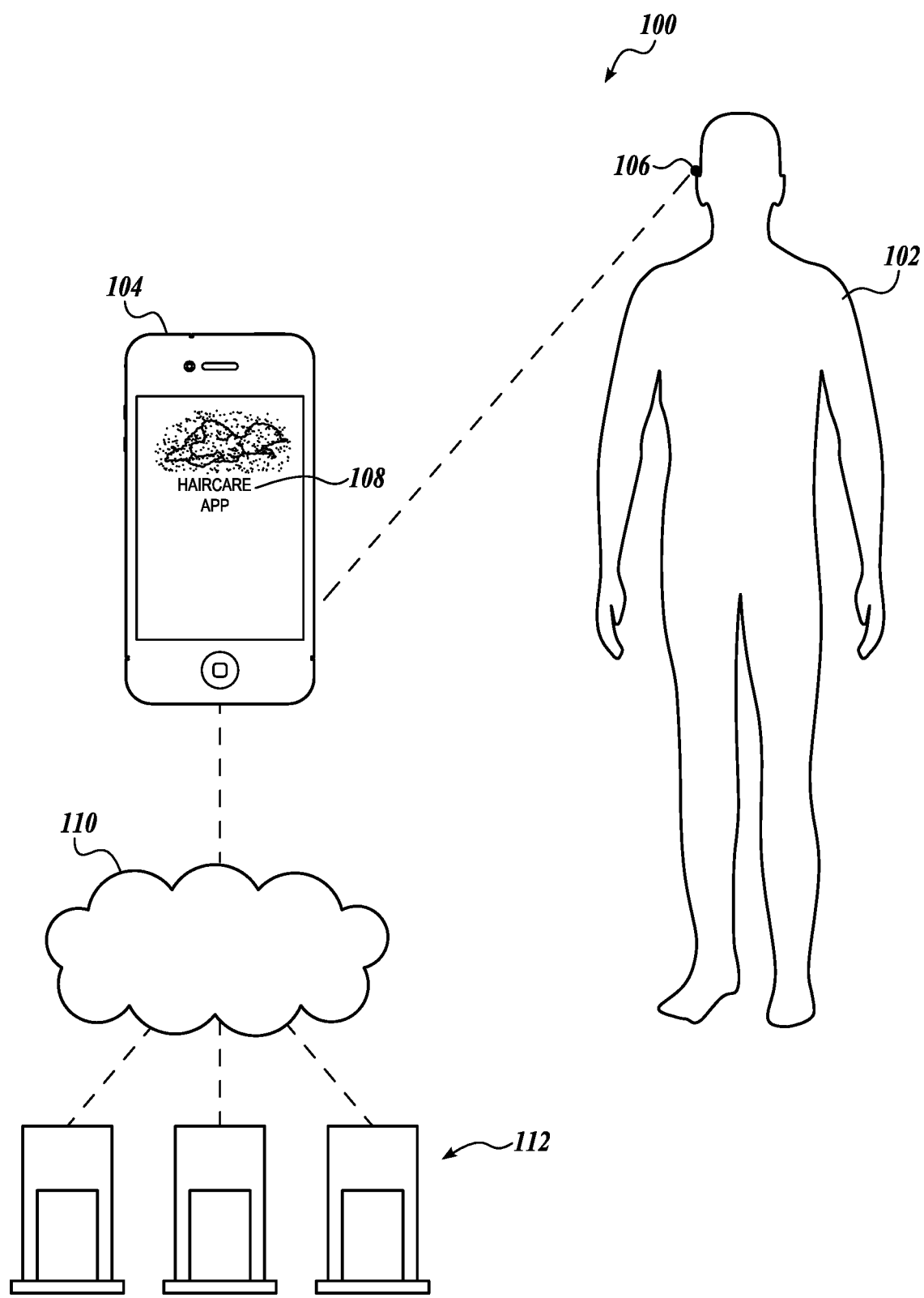
FIG. 1 a schematic diagram that illustrates one embodiment of a system for generating and providing haircare recommendations to a subject.

High levels of different types of light indoors or outdoors can detrimentally affect one's hair. Accordingly, one embodiment of the present disclosure is directed to a computer-implemented method and the computer system to make it possible for a subject to understand the damage to hair that can be inflicted by the various type of light, notifying a subject when possible damage to hair has occurred, and recommending one or more products to mitigate and remedy the hair damage.

As used herein, "light" denotes any radiation of any wavelength of the electromagnetic spectrum. In one embodiment, a light can have an adverse effect on a subject's hair. In one embodiment, different types of light include infrared, visible light, and ultraviolet. In one embodiment, light is radiation of any wavelength emitted by the sun.

In one embodiment, the present disclosure is directed to a computer system and computer-implemented method or App to educate and alert subjects about their exposure (real-time/hourly/daily/lifetime, etc.) to the full range of indoor and outdoor environmental factors, such as harmful light, that can damage their hair.

Air-borne pollutants, such as particulate matter (e.g., soot and heavy metals) and volatile organic gases (VOCs) can cause weakened hair that can break. Some hair sprays and other products, as well as the styling method (heat) may even exacerbate these conditions. Studies have also shown that the sunlight can lead to hair damage. The hair damage is not always the same for each person. Sunlight can cause degradation of proteins in hair, and loss of hair pigment. Generally, however, morphological damage, such as protein degradation is caused by exposure to UVB, and biochemical damage, such as color loss, is caused by exposure to UVA. Again, not every person will experience the same damage from the same type and amount of exposure to UVA, UVB, and visible light. For example, studies have also determined that hair damage caused from UVA and UVB is dependent on the hair type, such as color, composition, melanin content, waviness versus straight hair, etc. For each hair type, for example, there can be a different exposure limit at which UV can bleach or fade hair color. The exposure limits can be set to ensure that neither dyed or naturally colored hair does not lose color (and possibly texture). Beyond UV, there are potentially consequences for both hair and hair product (its efficacy and texture) when exposed to infrared light (heat).

Accordingly, one embodiment of this disclosure is to quantify hair damage according to hair type based on the amount of exposure to one or more types of light. In one embodiment, exposure can be defined as the intensity of the light over time.

In one embodiment, the present disclosure is directed to a computer system and computer-implemented method to provide subjects with more information on their exposure levels to harmful types of light as they move through different environments in their daily lives. In one embodiment, the subjects are informed about the harmful effects to allow the subject to purchase a wider range (a set) of hair products specifically targeted to correct or protect against the various effects. In one embodiment, the present disclosure is directed to a computer system and computer-implemented method to guide the subject on haircare products that are tailored to their lifestyle.

FIG. 1 is a schematic diagram that illustrates a one embodiment of a system 100 for tracking a subject's exposure time to one or more types of light, assessing damage to the subject's hair inflicted by the one or more types of light, and recommending a personalized set of haircare products depending on the damage caused by the types of light, and recommending a haircare product and regimen to prevent or alleviate damage caused by the one or more types of light.

In the system 100, the subject 102 interacts with a mobile computing device 104. In one embodiment, the mobile computing device 104 may be used to receive exposure data of one or more types of light from a wearable UV sensor 106 on the subject 102, additionally or alternatively, the data may come from one or more sources on the Internet, for example, online sources can report the air quality for a particular location, for example, online sites can provide the amount of ozone (O3), particulate matter (PM), sulfur dioxide (SO2), nitrogen dioxide (NO2) and nitrogen oxides (NOx), UVA, and UVB light.

In one embodiment, the mobile computing device 104 is capable of performing the computer-implemented method designated by the Haircare App icon 108. The subject may start the computer-implemented method by touching the icon 108 on a touch-sensitive display of the mobile computing device 104. The computer-implemented method is further described in connection with FIG. 4.

The personal, wearable environmental sensor 106 is for measuring different types of light radiation (i.e. UV-A, UV-B, Blue HEV, IR) and air-borne pollutants (i.e., CO, CO2, NO2, NOx, SO2, O3, PM2.5, PM10, VOC, heavy metals, radiation) as well as environmental factors, such as temperature and humidity. The amount of light radiation of different types and air-borne pollutants at given locations is also available for downloading from various publicly accessible sources on the Internet. In one embodiment, the sensor 106 is worn on or closer to the head to more accurately sense the amount of types of light impacting the subject's hair. The sensor 106, for example, can be integrated into eyewear or an earpiece worn by the subject 102. If, for example, the subject 102 is wearing a head covering, the sensor 106 can more accurately measure the types of light impacting on the hair, when the sensor is worn on the subject's head.

In one embodiment, the amount of one or more types of light in any environment is transmitted from the sensor 106 via a wireless technology to the mobile phone 104 running the Haircare App. The Haircare App receives these constantly changing values based on the subject's location and integrates them over time to calculate the type and amount that hair has been impacted by types of light, determines whether or not the subject's hair has been damaged or is at risk of being damaged, and alerts the subject accordingly.

In one embodiment, the mobile computing device 104 is connected to a remote server computer system 112 comprised of one or more server computers via a network, such as the Internet 110. The network may include any suitable networking technology, including but not limited to a wireless communication technology (including but not limited to Wi-Fi, WiMAX, Bluetooth, 2G, 3G, 4G, 5G, and LTE), a wired communication technology (including but not limited to Ethernet, USB, and FireWire), or combinations thereof.

Figure 2:
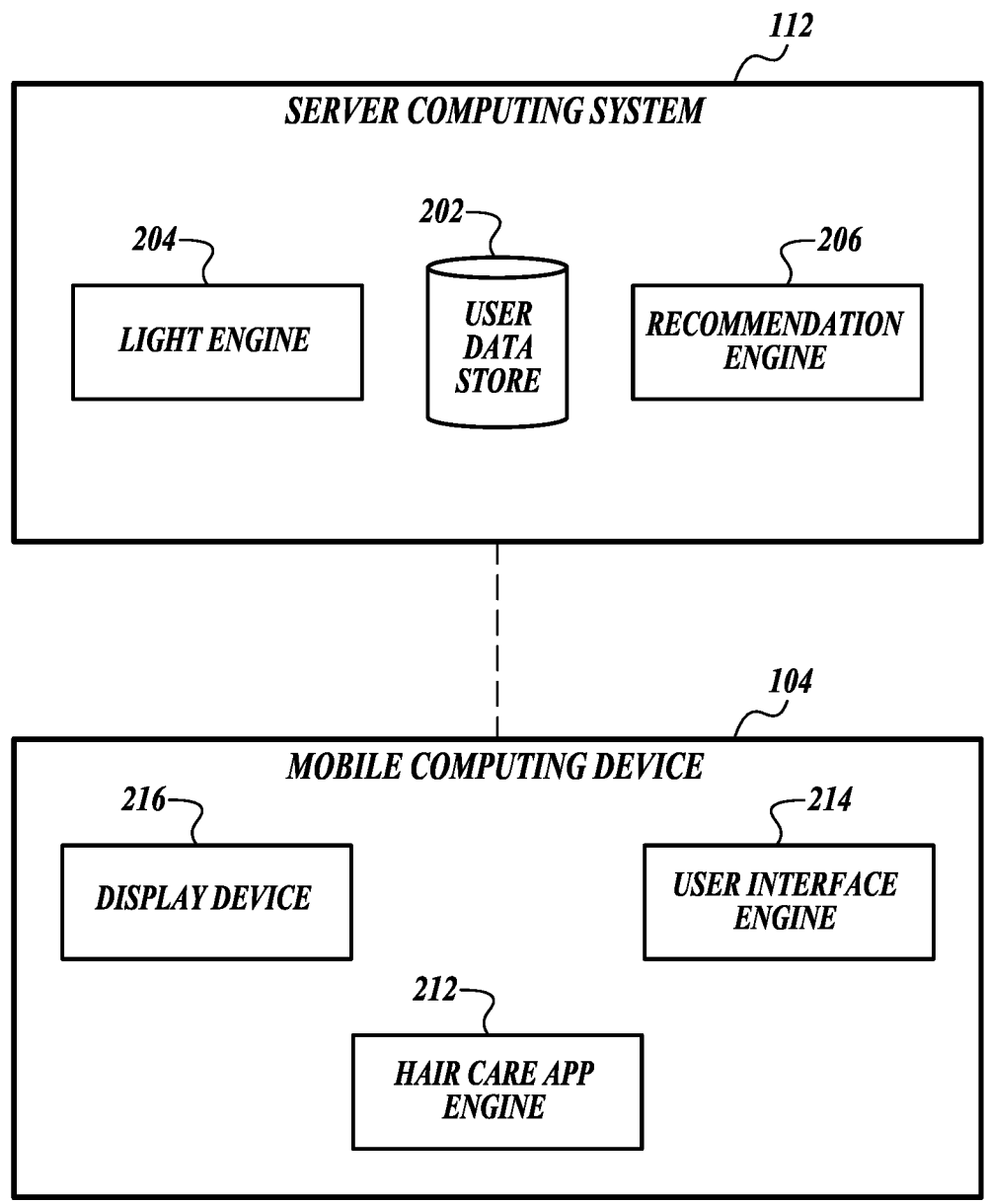
FIG. 2 is a block diagram that illustrates one embodiment of a system that includes a mobile computing device and a server computing device.

FIG. 2 is a block diagram that illustrates a non-limiting example embodiment of a system that includes the mobile computing device 104 and a server computing system 112 according to various aspects of the present disclosure. In one embodiment, the mobile computing device 104 may be a smartphone. In one embodiment, the mobile computing device 104 may be any other type of computing device having the illustrated components, including but not limited to a tablet computing device or a laptop computing device. In one embodiment, the mobile computing device 104 may not be mobile, but may instead be a stationary computing device, such as a desktop computing device. In one embodiment, the illustrated components of the mobile computing device 104 may be within a single housing. In one embodiment, the illustrated components of the mobile computing device 104 may be in separate housings that are communicatively coupled through wired or wireless connections. The mobile computing device 104 also includes other components that are not illustrated, including but not limited to one or more processors, a non-transitory computer-readable medium, a power source, and one or more communication interfaces.

As shown, the mobile computing device 104 includes, at least, a display device 216, a Haircare Application engine 212 (Haircare App engine 212), and a user interface engine 214.

In one embodiment, the display device 216 is an LED display, an OLED display, or another type of display for presenting a user interface. In one embodiment, the display device 216 may be combined with or include a touch-sensitive layer, such that a subject 102 may interact with a user interface presented on the display device 216 by touching the display. In one embodiment, a separate user interface device, including but not limited to a mouse, a keyboard, or a stylus, may be used to interact with a user interface presented on the display device 216.

In one embodiment, the user interface engine 214 is configured to present a user interface on the display device 216 when opening the Haircare App engine 212. The Haircare App engine 212 will cause the user interface engine 214 to display a plurality of user interfaces on the display device 216 relating to a computer-implemented method used for the gathering and display of information, including recommending a personalized set of haircare products depending on a damage assessment of hair based on the subject's profile, including hair type and based on the type and amount of light to which the subject's hair has been exposed.

In one embodiment, the user interface engine 214 can present the subject with a questionnaire that is useful to elicit information for determining the subject's profile, such as, but not limited to daily, weekly, and monthly schedules, hair type which can be selected from predetermined menu choices, haircare products currently used, hair styling methods currently used, but also provide other options and information.

In one embodiment, the server computing system 112 includes one or more computing devices that each include one or more processors, non-transitory computer-readable media, and network communication interfaces that are collectively configured to provide the illustrated components. In one embodiment, the one or more computing devices that make up the server computing system 112 may be rack-mount computing devices, desktop computing devices, or computing devices of a cloud computing service.

As shown, the server computing system 112 includes a user data store 202, a light engine 204, and a recommendation engine 210. In one embodiment, the server computing system 112 is configured to perform data analytics for determining the light intensity as a subject's location changes, integrating the light intensity over time, comparing the light exposure to target exposure levels for each type of light, determining the types of light to which the subject has the highest exposure, determining an assessment of the hair damage inflicted by the exposures, and making product recommendations. In one embodiment, the mobile computing device 104 is configured to connect to the server computing system 112 in a cloud computing environment to enable the mobile computing device 104 with the Haircare App engine 212 to use the computing resources of the server computing system 112. In one embodiment, one, some or all of the components of the user data store 202, light engine 204 and a recommendation engine 210 can reside in the mobile computing device 104.

In one embodiment, the user data store 202 is configured to store records for each subject 102 that uses the system. The records may the subject's profile including medical or personal records, such as age, weight, hair type, residence, occupation, athletic activities, schedules, past product recommendations, descriptions of lifestyle, and/or other information collected or determined by the system.

In one embodiment, the user data store 202 may also contain a database of haircare products, wherein each haircare product is identified by or classified according to one or more attributes. For example, a haircare product can be classified as having one or more of the following attributes: a UV blocker, a moisturizer, a humectant, antioxidant source, hyaluronic acid source, collagen source. In this manner, the recommendation engine 210 can recommend products that more precisely are directed to the type of damage caused by a particular light type.

In one embodiment, the user data store 202 may also contain a database of hair types. Hair types may be grouped according to color, composition, melanin content, or any combination of two or more factors. Each subject will be assigned one or more hair types. Each hair type can be related through a series of Tables that relate the hair type to the damage that is inflicted by each type of light and the exposure amount of each type of light. For example, a Table can quantify the type and amount of damage caused by a certain light type according to the amount of exposure to such light type for each hair type or combination of hair type. A Table has the exposure limits at which a light type is capable of inflicting hair damage. For each hair type, for example, there can be a different exposure limit at which UV can bleach or fade hair color. The exposure limits can be set to ensure that neither dyed or naturally colored hair does not lose color (and possibly texture). Beyond UV, there are potentially consequences for both hair and hair product (its efficacy and texture) when exposed to infrared light (heat). As can be appreciated there can be a multiplicity of Tables for each hair type to cover each light type and the exposure amount of light. The Tables also quantify the hair damage, so that a haircare product can be recommended that is specifically targeted to repair the damage.

In one embodiment, the light engine 204 may be configured to process the data acquired by a wearable light sensor 106 to determine light type levels and exposure times of the subject's hair to one or more types of light. In one embodiment, the light engine 204 may be configured to process the data acquired by online sources reporting the amount of different types of light at the given location of the subject. In one embodiment, the light engine 204 may be configured to both process the data acquired by the light sensor 106 and data acquired through online sources. In one embodiment, the light engine 204 may be configured to calculate the amount of light exposure on a minute, hourly, daily, weekly, monthly, yearly, or lifetime basis. In one embodiment, the light engine 204 calculates the light type levels by keeping track of a subject's location by global positioning system (GPS) coordinates.

In one embodiment, the light engine 204 is configured to calculate the subject's exposure to one or more types of light and integrate the exposure amount over time to determine a total exposure level. The total exposure level can then be compared to the relationship Tables that describe the damage to each particular hair type by type and amount of light. This comparison can be done on an hourly, daily, weekly, monthly, or yearly basis to continually update recommendations for haircare products as more exposure time to types of light leads to greater and greater damage to one's hair.

In one embodiment, the light engine 204 does not use the same target exposure limits for each subject. In one embodiment, the light engine 204 can adjust the target exposure limit based on each subject's profile, and in particular, the subject's hair type. Additionally, other factors in a subject's profile may be used to increase or decrease target exposure limits for a type of light to deem when hair damage has occurred.

In one embodiment, the exposure limits of pollutants are adjusted based on the interaction between light, such as UV, and other pollutants. For example, while light can lead to a hair damaging effect, the effect can be multiplied through the presence of air-borne pollutants. Also, because light of a certain wavelength and pollutants can independently lead to similar hair damage effects, if the light exposure limit is related to the onset of these effects, then prior pollutant exposure having similar hair damaging effects can reduce the light exposure limit, and visa-versa. In other words, air-borne pollutants can have the same hair damaging effect as light, and the light exposure limit should be determined based on the combined exposure of the light and the pollutant. Therefore, in one embodiment, the exposure limits of light types are adjusted down based the amount of pollutant exposure of the subject or the light type exposure limit is based on counting both the amount of exposure of the light type as well as the amount of exposure to one or more pollutants that has the same hair damaging effect as the light type. The compounding effect is not limited to pollutants, but, can also include other light types that have the same hair damaging effect. In other words, light type exposure limits are based on counting the exposure amounts of more than one light type. In this case, there is a total exposure limit for a group of light types that have the same hair damaging effect. In one embodiment, the exposure limit of a light type or a group of light types is a sum total based on counting the exposure amounts of the all the light types that have the same damaging hair effects. In one embodiment, the amount of exposure of light types that contribute to the same hair damaging effect can be weighted according to the proportional contribution each light type has to cause the hair damaging effect.

The light engine 204 uses the subject's profile, including hair type, such as color and melanin type and content or other attributes to set the target exposure limit.

In one embodiment, the recommendation engine 210 is configured to generate recommendations of haircare products for protection against one or more types of light or for care of damaged hair caused by light. In one embodiment, the recommendation engine 210 provides a set of haircare product recommendations based an assessment of the damage done to hair based on the types of light to which the subject has the highest exposure.

In one embodiment, the recommendation engine 210 can further calculate recommendations based on the subject's profile, such as currently used products and styling methods. In this manner, the recommendation engine 210 is able to provide a personalized set of haircare products unique to the subject.

In one embodiment, products for recommendations are stored in a manner that associates the products' qualities to the hair damage the product aims to repair or alleviate. In this way, once hair damage is calculated, an appropriate product can be recommended.

In one embodiment, haircare products may include water-based shampoos or dry shampoos. Haircare products may also include other ingredients, such as UV blockers, moisturizers, humectants, antioxidants, hyaluronic acid, collagen, EDTA, carriers such as oil and water, and the like. In one embodiment, a haircare product is categorized according to the damage it is aimed to help. The products can be associated with the Tables that show relationships between hair type, the types of light, and hair damage inflicted by types of light.

"Engine" refers to logic embodied in hardware or software instructions, which can be written in a programming language, such as C, C++, COBOL, JAVA™, PHP, Perl, HTML, CSS, JavaScript, VBScript, ASPX, Microsoft. NET™, Go, and/or the like. An engine may be compiled into executable programs or written in interpreted programming languages. Software engines may be callable from other engines or from themselves. Generally, the engines described herein refer to logical modules that can be merged with other engines, or can be divided into sub-engines. The engines can be stored in any type of computer-readable medium or computer storage device and be stored on and executed by one or more general purpose computers, thus creating a special purpose computer configured to provide the engine or the functionality thereof.

"Data store" refers to any suitable device configured to store data for access by a computing device. One example of a data store is a highly reliable, high-speed relational database management system (DBMS) executing on one or more computing devices and accessible over a high-speed network. Another example of a data store is a key-value store. However, any other suitable storage technique and/or device capable of quickly and reliably providing the stored data in response to queries may be used, and the computing device may be accessible locally instead of over a network, or may be provided as a cloud-based service. A data store may also include data stored in an organized manner on a computer-readable storage medium, such as a hard disk drive, a flash memory, RAM, ROM, or any other type of computer-readable storage medium. One of ordinary skill in the art will recognize that separate data stores described herein may be combined into a single data store, and/or a single data store described herein may be separated into multiple data stores, without departing from the scope of the present disclosure. In one embodiment, the data store 202 is used for storing the relationship Tables that link subjects' profiles, hair type, light type, hair damage, and haircare products, which are then used in making assessments of hair damage and providing haircare product recommendations according to specific hair types.

Figure 3:
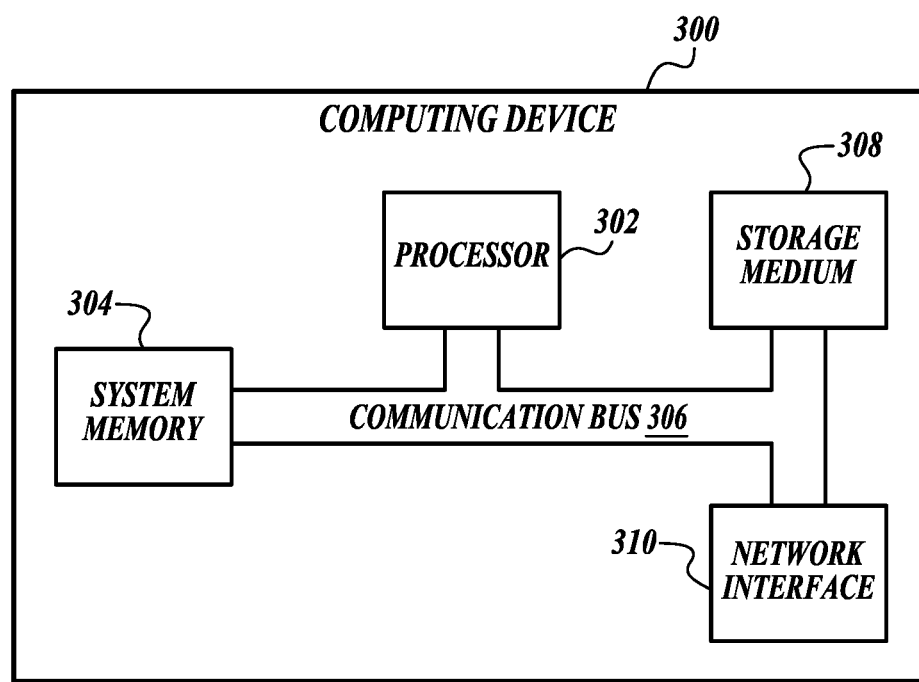
FIG. 3 is a block diagram that illustrates one embodiment of a computing device appropriate for use as a computing device with embodiments of the present disclosure.

FIG. 3 is a block diagram that illustrates aspects of an exemplary computing device 300 appropriate for use as a mobile computing device of the present disclosure. While multiple different types of computing devices were discussed above, the exemplary computing device 300 describes various elements that are common to many different types of computing devices. While FIG. 3 is described with reference to a mobile computing device, the description below is applicable to servers, personal computers, mobile phones, smart phones, tablet computers, embedded computing devices, and other devices that may be used to implement portions of embodiments of the present disclosure. Moreover, those of ordinary skill in the art and others will recognize that the computing device 300 may be any one of any number of currently available or yet to be developed devices.

In its most basic configuration, the computing device 300 includes at least one processor 302 and a system memory 304 connected by a communication bus 306. Depending on the exact configuration and type of device, the system memory 304 may be volatile or nonvolatile memory, such as read only memory ("ROM"), random access memory ("RAM"), EEPROM, flash memory, or similar memory technology. Those of ordinary skill in the art and others will recognize that system memory 304 typically stores data and/or program modules that are immediately accessible to and/or currently being operated on by the processor 302. In this regard, the processor 302 may serve as a computational center of the computing device 300 by supporting the execution of instructions.

As further illustrated in FIG. 3, the computing device 300 may include a network interface 310 comprising one or more components for communicating with other devices over a network. Embodiments of the present disclosure may access basic services that utilize the network interface 310 to perform communications using common network protocols. The network interface 310 may also include a wireless network interface configured to communicate via one or more wireless communication protocols, such as WiFi, 2G, 3G, LTE, WiMAX, Bluetooth, Bluetooth low energy, and/or the like. As will be appreciated by one of ordinary skill in the art, the network interface 310 illustrated in FIG. 3 may represent one or more wireless interfaces or physical communication interfaces described and illustrated above with respect to particular components of the computing device 300.

In the exemplary embodiment depicted in FIG. 3, the computing device 300 also includes a storage medium 308. However, services may be accessed using a computing device that does not include means for persisting data to a local storage medium. Therefore, the storage medium 308 depicted in FIG. 3 is optional. In any event, the storage medium 308 may be volatile or nonvolatile, removable or nonremovable, implemented using any technology capable of storing information such as, but not limited to, a hard drive, solid state drive, CD ROM, DVD, or other disk storage, magnetic cassettes, magnetic tape, magnetic disk storage, and/or the like.

As used herein, the term "computer-readable medium" includes volatile and non-volatile and removable and non-removable media implemented in any method or technology capable of storing information, such as computer readable instructions, data structures, program modules, or other data. In this regard, the system memory 304 and storage medium 308 depicted in FIG. 3 are merely examples of computer-readable media.

Suitable implementations of computing devices that include a processor 302, system memory 304, communication bus 306, storage medium 308, and network interface 310 are known and commercially available. For ease of illustration and because it is not important for an understanding of the claimed subject matter, FIG. 3 does not show some of the typical components of many computing devices. In this regard, the computing device 300 may include input devices, such as a keyboard, keypad, mouse, microphone, touch input device, touch screen, tablet, and/or the like. Such input devices may be coupled to the computing device 300 by wired or wireless connections including RF, infrared, serial, parallel, Bluetooth, Bluetooth low energy, USB, or other suitable connections protocols using wireless or physical connections. Similarly, the computing device 300 may also include output devices such as a display, speakers, printer, etc. Since these devices are well known in the art, they are not illustrated or described further herein.

Figure 4:
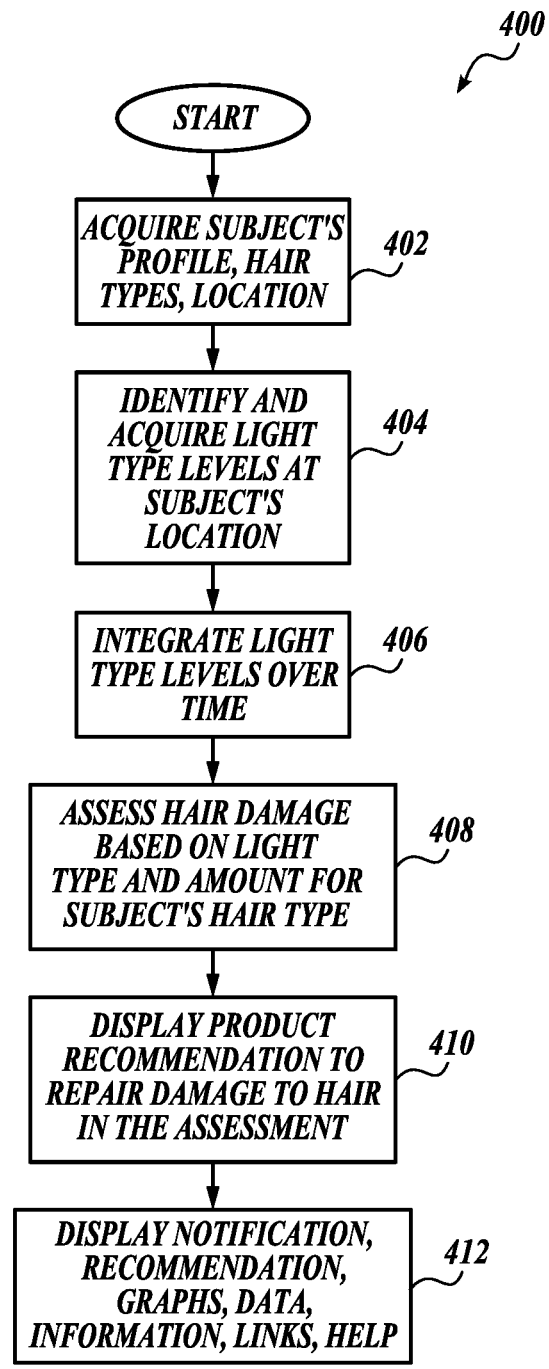
FIG. 4 is a flowchart that illustrates one embodiment of a method of generating and providing recommendations to a subject.

FIG. 4 is a flowchart that illustrates a non-limiting example embodiment of a computer-implemented method of recording the type and amount of light to which a subject with a particular hair type has been exposed, assessing the damage inflicted by the particular type and amount of light, and then, recommending a haircare product directly targeted to repair the specific hair damage. In one embodiment, a damage assessment of hair takes into consideration the subject's profile, including for example, hair type or other attributes in the subject's profile. The method 400 may be implemented, in one example, by the mobile computing device 104 alone or in combination with one or more server computing devices 112. The computer-implemented method is performed by the Haircare App engine 212, light engine 204, recommendation engine 210, user interface engine 214 communicating with each other and with the user data store 202.

In one embodiment, the method may be performed in part by the mobile computing device 104 and in part by the remote server computer system 112. In one embodiment, the mobile computing device 104 is configured to upload data regarding the subject to an external system or server (such as a cloud-based system). Such data may include the subject profile. In one embodiment, a subject profile includes the subject's hair type, such as color, composition, melanin types and content, and the like, and haircare product currently used by the subject, and any current styling regimens used by the subject.

The computer-implemented method 400 may start by clicking on the Haircare App icon 108 on the display of the mobile computing device 104 to open the Haircare App engine 212.

From the start block, the Haircare App engine 212 proceeds to block 402, where the Haircare App engine 212 receives the subject's 102 profile, location, and hair type, for example.

If a profile has not been provided, the Haircare App engine 212 can use the user interface engine 214 to present to the subject, a questionnaire with questions regarding all the relevant information needed to complete the profile. The subject can enter the information through the display device 216 thought the use of menu with preselected lists of choices. In one embodiment, the Haircare App engine 212 accesses the user data store 202 for the profile and other information.

In one embodiment, the subject's location can be constantly determined through a GPS in the mobile computing device 104. In this way, the subject's location can be continuously monitored and updated in real time. In one embodiment, the location is used to retrieve information about the light type levels at that subject's current location. The current location can be continuously updated as the subject moves from location to location.

In block 404, the light engine 204 identifies the type of light the subject's hair is currently being exposed to, the light type level, and begins to record the exposure time for each light type as the subject moves from location to location. More specifically, the light engine 204 identifies the types and amount of light impacting hair on a subject. In order to obtain more accurate results, the sensor 106 may be worn on or closer to the head, such as on eyeglasses, an ear piece, or clipped to a piece of clothing worn on or close to the subject's hair. Further, if the subject is wearing a hat or otherwise shielding his or her hair form exposure, the light engine 204 has a way to adjust the light type exposure amount by taking into consideration the type of head covering being used or the sensor 106 is also being shielded by the head covering so the sensor correspondingly senses less exposure.

In one embodiment, the amount and types of light can be retrieved from publicly accessible online sources on air quality by selecting those sources within a radius of the subject's GPS location or the amount of light can be determined by one or more sensors 106 worn by the subject 102 or placed on the mobile computing device 104. Depending on the sensor 106, data can be processed by the sensor 106 or the mobile computing device 104. In one embodiment, the subject 102 scans the sensor 106 with the mobile computing device 104 to establish a connection between the sensor 106 and the mobile computing device 104. Communication pairing is performed between the sensor 106 and the mobile computing device 104 when the two devices are within an acceptable wireless communication range of each other. In one embodiment, the sensor 106 includes RFID and antenna for the subject to obtain the data wirelessly.

To illustrate how a light sensor may operate, an example is provided where the sensor 106 is a UV sensor that contains a UV sensitive LED that will induce electronic current proportional to UV intensity. The amount of UV exposure can then be converted and stored as voltage, which is a measurement of cumulative UV exposure over time. UV exposure can be reported on a per unit of time basis, such as daily, weekly, monthly, etc. The voltage is read each time as the subject scans the sensor 106. The scanned voltage data is converted into a UV-A dosage based on the calibrated correlations. In one embodiment, UV-B exposure is then calculated using a pre-computed lookup table that gives the conversion factor as function of the column amount of ozone in the atmosphere and solar zenith angle (SZA). SZA is determined based on GPS location and time. Other sensors capable of measuring the amount of other types of light can be similarly configured to be read by the mobile computing device 104. From block 404, the method proceeds to block 406.

In block 406, whether the light engine 204 receives the light type levels from sensors 106 or online sources, the light engine 204 keeps track of the light type levels at the subject's location and the time at the location to integrate the light type level of each light type into a running exposure amount over time. In this manner, the light engine 204 can keep track of the subject's location and the light type levels at each location throughout the subject's daily routine. This can be done automatically by the mobile computing device 104, or the subject can decide when to turn the Haircare App engine 212 on and off. The subject 102 can also follow their light type level exposure over time. The light engine 204 can keep a running total of light type exposure in any increments of time, such as by the minute, hour, day, week, month, or year. From block 406, the method proceeds to block 408.

In block 408, the light engine 204 assesses the damage inflicted on the subject's hair by considering the type and amount for each light type. The damage assessment may be performed through the use of data Tables that store relationships of the damage caused by each light type for each hair type. Hair types may be grouped according to color, composition, melanin content, or any combination of two or more factors. The Tables may also store incremental damage caused by higher exposure of each type of light. The Tables contain the light type exposure targets that determine hair damage has occurred for each light type.

In one embodiment, the light type exposure limit is the amount of a given light type that when considered alone leads to hair damage. However, hair damage effects can be the result of more than one light type. The light engine 206 can take other factors to derive light type exposure limits. In one embodiment, the exposure limits of light types are adjusted based on the interaction between the light type and air-borne pollutants. Also, because light and pollutants can independently lead to similar hair damage effects, if the light type exposure limit is related to the onset of these effects, then prior pollutant exposure can reduce the light type exposure limit, and visa-versa. Therefore, in one embodiment, the exposure limits of light types are adjusted down based the amount of pollutant exposure of the subject to pollutants having similar hair damaging effects or the light type exposure limit is based on counting both the exposure of the light type as well as the exposure to pollutants that have the same hair damaging effect as the light type. In one embodiment, the light type exposure limit is a sum total of the exposure amounts of light types and pollutants that have the same hair damaging effect.

A Table can quantify greater damage according to greater exposures to different types of light, and consequently recommend higher doses or increase the frequency of treatments with haircare products. Tables may also store any damage that is the caused by two or more types of light. In performing a hair damage assessment, the light engine 204 uses the subject's profile, including hair type or other attributes personal to the subject, the type and amount of each light type, and then, uses the Tables to find the type of hair damage inflicted by the types of light. From block 408, the method enters block 410.

In block 410, the recommendation engine 210 can display a notification to the subject detailing the light type exposure and the damage being caused to the hair. In one embodiment, the user interface engine 214 may display the recommended haircare products based on the hair damage assessment. The Tables storing the hair damage related by type and amount of light type exposure can also store the product or products that aim to help repair the hair damage. In one embodiment, the user interface engine 214 can display the type of hair damage, its causes, helpful information, and the like. In one embodiment, the user interface engine 214 creates tutorials on how to use the haircare products. The user interface engine 214 may create and download protocols for a regimen or routine on how to use the haircare products. The user interface engine 214 may can coach, track usage and compare the tracked usage to the protocol, the regimen, and the routine. Therefore, the Haircare App 212 can keep track of each subject's profile and light type exposure levels and can provide recommendations on product selection, styling methods, haircare regimens that are based on the levels of types of light that can damage hair, an assessment of damage caused to particular hair types by the type and exposure amounts according to individual types of light. Additionally, the user interface engine 214 can be used to make a purchase of any products related to the recommended haircare products. From block 410, the method proceeds to block 412.

In block 412, the user interface engine 214 can display helpful graphs, data, information, warnings, useful links, and help relating to the hair damage and the types of light. In one embodiment, the user interface engine 214 may create a display on the mobile computing device 104 with an indication of the subject risk of hair damage in percentage form, along with a category label such as "low", "moderate," or "high." A graph may also be displayed that tracks the light type exposure levels over time. The subject may recall any prior history on exposure levels for the types of light.

In one embodiment, the computer-implemented method 400 is continuously running to update the types of light and the integrated amount of exposure to different types of light over time to update its hair damage assessment and make new or updated recommendations.

While illustrative embodiments have been illustrated and described, it will be appreciated that various changes can be made therein without departing from the spirit and scope of the invention.

The embodiments of the invention in which an exclusive property or privilege is claimed are defined as follows:

1. A system comprising a light sensor and a smartphone, comprising:
the sensor includes;
a UV sensitive LED that induces an electronic current proportional to UV intensity, wherein the amount of UV exposure is converted and stored as voltage;
the smartphone includes:
wireless communication; and
a computer-readable medium having stored thereon instructions that execute steps to:
read the voltage data from the sensor and convert the data into a UV-A dosage, and convert the UV-A dosage into a UV-B exposure using a pre-computed lookup table that gives the conversion factor as function of the column amount of ozone in the atmosphere and solar zenith angle;
create a subject profile of a subject wearing the sensor, wherein the subject profile includes one or more of hair type, hair color, hair composition, and melanin type and content in hair;
calculate a target exposure limit for UV-B at which a harmful hair effect occurs based on the subject profile, wherein the harmful hair effect is related to one or more of degradation of proteins in hair or loss of hair pigment;
communicate wirelessly with the sensor to determine an exposure amount of UV- B impacting the subject's hair when the sensor is scanned using the smartphone;
determine whether the amount of UV-B exposure exceeds the target exposure limit;
provide a notification when the exposure exceeds the target exposure limit; and
provide at least one haircare product recommendation to the subject, wherein the haircare product includes one or more of UV blockers, moisturizers, humectants, antioxidants, hyaluronic acid, collagen, and EDTA to repair damage to the hair.

2. The system of claim 1, wherein the at least one haircare product recommendation is a personalized recommendation based on a subject's profile including styling methods used by the subject.

3. The system of claim 2, wherein the subject's profile includes haircare products currently used by the subject.

4. The system of claim 1, wherein the computer-readable medium further has stored thereon instructions that execute steps to track exposure amounts of IR and Blue HEV.

5. The system of claim 4, wherein the computer-readable medium further has stored thereon instructions that execute steps to continuously integrate a total amount of exposure for each type of light impacting the subject's hair.

6. The system of claim 4, wherein the computer-readable medium further has stored thereon instructions that execute steps to further determine the target exposure limit based on an airborne pollutant interacting with UV-B or determine the target exposure limit based on a sum total of exposure amounts of UV-B and one or both of IR and Blue HEV.

* * * * *